(12) United States Patent
Schmid et al.

(10) Patent No.: US 10,849,491 B2
(45) Date of Patent: *Dec. 1, 2020

(54) METHOD AND DEVICE FOR DETERMINING THE VISUAL ACUITY OF A USER

(71) Applicant: Oculocare Medical AG, Zürich (CH)

(72) Inventors: Martin K. Schmid, Lucerne (CH);
Michael A. Thiel, Nürensdorf (CH);
Lucas M. Bachmann, Zürich (CH);
Kenny R. Lienhard, Lausanne (CH)

(73) Assignee: Oculocare Medical AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/590,934

(22) Filed: Oct. 2, 2019

(65) Prior Publication Data

US 2020/0129059 A1    Apr. 30, 2020

Related U.S. Application Data

(63) Continuation of application No. 15/570,566, filed as application No. PCT/EP2016/058911 on Apr. 21, 2016, now Pat. No. 10,470,654.

(30) Foreign Application Priority Data

Apr. 30, 2015  (EP) .................................... 15166029

(51) Int. Cl.
*A61B 3/032* (2006.01)
*A61B 3/00* (2006.01)
*A61B 3/14* (2006.01)

(52) U.S. Cl.
CPC ............ *A61B 3/032* (2013.01); *A61B 3/0025* (2013.01); *A61B 3/0041* (2013.01); *A61B 3/14* (2013.01); *A61B 2560/0431* (2013.01)

(58) Field of Classification Search
CPC .......... A61B 3/00; A61B 3/032; A61B 3/0025; A61B 3/0041; A61B 3/14; A61B 3/103;
(Continued)

(56) References Cited

U.S. PATENT DOCUMENTS 4,798,456 A      1/1989  Enoch et al.
10,470,654 B2 * 11/2019  Schmid ................ A61B 3/0025
(Continued)

FOREIGN PATENT DOCUMENTS

JP        2005517482 A     6/2005
JP        2014533587 A    12/2014
(Continued)

OTHER PUBLICATIONS

English Translation of International Preliminary Report on Patentability dated Nov. 9, 2017 in counterpart international application No. PCT/EP2016/058911.
(Continued)

*Primary Examiner* — Jie Lei
(74) *Attorney, Agent, or Firm* — Sughrue Mion, PLLC

(57) ABSTRACT

A method for determining the visual acuity, wherein two spaced outer markings and an orientation marking lying between but not on a straight connecting line are displayed to the user on a display in an individual test as part of a plurality of tests. The user is to move the orientation marking on the display perpendicularly to the straight connecting line by actuating the device until the user perceives the marking as lying on the straight connecting line. Afterwards, the electronic device registers the effective distance between the orientation marking and the connecting line. At least two tests are carried out in which the outer markings are arranged along the same main axis, and at least the vertical main axis and the horizontal main axis are measured. After the
(Continued)

manipulation, the effective distance from the individual tests of the series is used for ascertaining the visual acuity.

31 Claims, 3 Drawing Sheets

(58) Field of Classification Search
CPC .. A61B 3/152; A61B 3/113; A61B 2560/0431
USPC ....... 351/205, 206, 208, 210, 211, 218, 223, 351/246
See application file for complete search history.

(56) References Cited

U.S. PATENT DOCUMENTS

| | | |
|---|---|---|
| 2005/0122477 A1 | 6/2005 | Alster et al. |
| 2012/0050685 A1 | 3/2012 | Bartlett et al. |
| 2013/0235346 A1 | 9/2013 | Huang |

FOREIGN PATENT DOCUMENTS

| | | |
|---|---|---|
| WO | 03070089 A1 | 8/2003 |
| WO | 2010/132304 A1 | 11/2010 |
| WO | 2013078406 A1 | 5/2013 |

OTHER PUBLICATIONS

International Search Report for PCT/EP2016/058911, dated Jun. 23, 2016 (PCT/ISA/210).

\* cited by examiner

METHOD AND DEVICE FOR DETERMINING THE VISUAL ACUITY OF A USER

CROSS REFERENCE TO RELATED APPLICATIONS

This is a Continuation of application Ser. No. 15/570,566 filed Oct. 30, 2017, claiming priority based on International Application No. PCT/EP2016/058911 filed Apr. 21, 2016, claiming priority based on European Patent Application No. 15 166 029.7, filed Apr. 30, 2015, the contents of all of which are incorporated by reference herein in their entirety.

TECHNICAL AREA

The present invention relates to a method and a device for determining the visual acuity of a user. In particular, it relates to a method which enables the user, independently and regularly without great effort, over a relatively long time and, for example, in the scope of a medical treatment, to check these functions, in order then to be able to seek medical aid in a timely manner if this is necessary.

PRIOR ART

Diverse methods are known from the prior art for checking or monitoring the visual acuity, respectively. Thus, for example, U.S. Pat. No. 4,798,456 describes a method, using which metamorphopsia can be measured quantitatively, by presenting different images to the affected person, and the person subsequently being questioned about the perception.

For example, a handheld eyesight tester and a method for self-testing of the sight of a user using such a device are known from WO2010132304. The method ensures that deviations from the permissible spacing are compensated for in a display of the handheld eyesight tester within an acceptable distance from the eye of the user. Various shapes are displayed on the display to the user, either dynamically or statically, in the scope of the method. The method also enables the input of reactions of the user to the various shapes, which are in turn displayed. Results of the self-test are determined from the reactions generated by the user. In this case, for example, circles are displayed adjacent to deformed circles, and the user has to identify the deformed circles.

A method for measuring the visual capacity of a user is known from U.S. Pat. No. 4,798,456, in which method two points, which are spaced apart but fixed in the position thereof, are specified and the patient is requested to displace a third point along the connecting axis of the two outer fixed points into the center between these two fixed points.

A method is known from US 2005/122477, in which method a test pattern is specified, and the user is requested to perform certain changes on this test pattern, and conclusions are drawn about the vision behavior of the user from the corresponding behavior feedback of the user. A similar method is known from US 2012/050685.

DESCRIPTION OF THE INVENTION

It is accordingly the object of the present invention to provide an improved method for determining the visual acuity (wherein this term is also to include the field of vision) of a user, which can be carried out in a reliable and error-free manner without medical assistance.

This object is achieved by a method as claimed in claim 1 or a data processing program for carrying out such a method, respectively, or by a mobile electronic device having such a method.

The proposed test is used to measure the capacity of the visual system. However, an inference can also be drawn indirectly, via the capacity of the visual system, about general capacities of the user, for example the response capacity, the strength, or the state of relaxation. Accordingly, a conclusion can also be drawn indirectly about the general physiological state, for example also the degree of alcoholization or in general the state under the influence of drugs or medications, under the influence of an illness which is possibly also not directly related to the eyes and the visual capacity, or a mental state, or a combination of these aspects. The method checks the capacity for registering points in the spatial relationship thereof in relation to one another. This quality of vision is known as so-called Vernier acuity. This visual capacity is based on the visual performance of the retina and higher-level structures in the visual signal processing. The accuracy of this visual performance can be influenced by various aging processes or pathological processes. These processes include age-related macular degeneration (AMD), diabetic retinopathy, vascular occlusions of any type in the retina and the optic tract, macular edema of any genesis (for example, postoperative, diabetic, inflammatory), diseases of the retina which result in displacement of the photoreceptors, for example epiretinal fibroplasia, vitreofoveal traction syndrome, and macular hole, as well as diseases of the optic nerve, for example glaucoma.

The location of the presented spots can be selected so that they are specifically placed on the affected points of the retina. The selection of the location of the points can be made on the basis of morphological examinations, for example optical coherence tomography (OCT) or on the basis of the results of prior examinations using the method described here (adaptive or learning method). In addition, upon repeated application, by way of the comparative analysis of the precision and the speed of the inputs and responses by the test person, the influence of daily performance variations or pathological changes of the brain on the type or speed of image perception or the influence of exogenous substances such as alcohol or other sedative and hallucinogenic substances on the response capacity of the brain can be measured. By way of the dynamic component of the Vernier acuity test, retina related and non-retina related changes or variations of the measurement results can be registered and the detection sensitivity of the system to functional changes of the retina can be increased.

Specifically, the present invention relates to a method for determining the visual acuity, in which the user completes a test series of multiple individual test procedures carried out in succession. In this case, in the scope of each individual test procedure, two spaced-apart outer marks, which are fixed within an individual test procedure, and an alignment mark located therebetween but not on a connecting straight line of the outer marks are displayed on a display screen of an electronic device. The user is now prompted, by actuating the electronic device, to displace the alignment mark on the display screen perpendicularly to the connecting straight line of the outer marks until in the perception of the user the alignment mark lies on the connecting straight line between the outer marks. In this manner, the user focuses his vision on the alignment mark, but has to position it relative to the outer marks.

Subsequently, after completed displacement of the alignment mark by the user, the electronic device registers and analyzes at least one of the following registered parameters:

the effective spacing of the alignment mark from the connecting straight line after displacement of the alignment mark by the user;

the time which the user has required for the displacement of the alignment mark;

the number of direction changes during the displacement of the alignment mark by the user.

The individual test procedure is typically ended by the user making a corresponding input, for example by the user acting on a field "continue" on the display screen.

In this case, typically at least two or at least three individual test procedures are carried out, in which the outer marks are arranged along the same main axis or previously determined auxiliary axes, and wherein at least two different main axes are measured in the scope of one test series. Subsequently, at least one of the registered parameters or, upon measurement of multiple parameters, preferably a combination of the registered parameters is used as a measure for determining the visual acuity from the individual test procedures of the test series.

Conventional measuring methods for determining the Vernier acuity, for example the Amsler grid, have the disadvantage that the tested person has to focus on a certain point, but is requested to assess visual impressions which are located outside the point focused on. In the method described here, the situation is more or less reversed, without the user noticing this, which substantially simplifies the reliability and the simplicity of the measurement.

The following definitions apply in conjunction with the present invention:

Electronic Device:

This is to be understood in general as a device which is capable of providing an image to a user. These are devices for monocular or binocular display of two-dimensional or three-dimensional images. These accordingly include mobile devices (for example tablets and smartphones) and personal computers (for example desktop computers and laptops), but also projectors, head-mounted devices, interactive spectacles, 3D display devices, holographic display devices, (large-scale) screens, data spectacles, data helmets, hologram lasers, etc.

Display Screen:

This is to be understood not only as a display screen in the classical meaning, but rather in general a device for displaying two-dimensional or three-dimensional images for one or both eyes. In other words, the term includes not only conventional display screens, but rather also displays projected on a surface, and also the display means as are used, for example, in data spectacles or in holographic displays. Display screens which are touch-sensitive are preferred.

Outer Marks:

The marks arranged outside the immediate visual area of attention of the user are referred to as outer marks, wherein the shape thereof is not specified further in principle, as long as they are capable of making an imaginary connecting straight line therebetween visually conceivable to the user. The outer marks, which can be formed, for example, as spots or strokes or also circles or triangles, can be supplemented or amplified by additional aids, for example circles or shading, etc.

Alignment Mark:

The display element between the outer marks is referred to as the alignment mark. This element of the alignment mark is also not specified further in principle with respect to shape, as long as it enables this outer mark to be positioned in the most comprehensible manner on the imaginary connecting straight line between the outer marks. Alignment mark and outer marks can be displayed more or less positively on a light background, but they also can be displayed more or less negatively on a dark background. A mixed display is also conceivable, i.e., the outer marks are displayed as darker marks on a medium background and the alignment mark as lighter markings, or vice versa.

Spacing:

The spacing of the alignment mark is to be understood as the spacing of the alignment mark from the imaginary connecting straight line between the two outer marks. The spacing is correspondingly equal to zero if the alignment mark is located precisely on the imaginary connecting straight line between the two outer marks. The spacing generally changes in the scope of an individual test procedure. Initially, an alignment mark which is not located on a connecting straight line of the outer marks is displayed between the outer marks, i.e., the spacing is not equal to zero initially, the dimension of the initial spacing is preferably specified randomly, wherein for this initial value typically an absolute minimum value and an absolute maximum value are set for this random specification. In the course of the individual test procedure, the user displaces the alignment mark along a direction perpendicular to the imaginary connecting straight line of the outer marks, he cannot displace the alignment mark at all along other axes, and at the end of the individual test procedure, a spacing results, which corresponds to the effective spacing of the alignment mark from the connecting straight line after displacement of the alignment mark.

Offset:

The offset of the alignment mark is the position of the alignment mark relative to the distance between the two outer marks. If one considers the imaginary connecting straight line between the two outer marks as the x axis and the axis perpendicular thereto as the y axis, the offset is thus accordingly the x coordinate of the alignment mark and the above-defined spacing of the alignment mark is they coordinate of the alignment mark.

The relationships are graphically shown in FIG. 1b for the situation of a horizontal main axis. The above-defined spacing corresponds to the dimension c in this figure, the distance between the outer marks 3 and 4 corresponds to d, and the dimension a corresponds to the offset. The alignment mark 5 can only be displaced along the displacement direction 16, which extends perpendicularly to the connecting straight line 6.

Main Axes:

The main axes are understood as the vertical axis (vertical main axis) and the horizontal axis (horizontal main axis), as they appear to the user upon the intended use of the display screen of the corresponding electronic device. The direction of the corresponding main axis corresponds to the imaginary connecting straight line between the two outer marks.

Diagonal Axes or Auxiliary Axes:

These additional axes are to be understood as axes which are arranged at an angle between the main axes. These auxiliary axes can be arranged at an angle of 45° in relation to the vertical or horizontal main axis, respectively, and can therefore be the axes conventionally designated as diagonal axes. However, diagonal axes according to the present invention are to be understood in general as axes which have an angular deviation sufficient for these applications from the vertical and the horizontal main axis. Typically, these diagonal main axes preferably enclose, independently of one another, an angle with the horizontal or vertical main axis, respectively, of 10-80°, preferably in the range of 20-70°, particularly preferably in the range of 30-60°. These diagonal main axes very particularly preferably enclose an angle with the horizontal or vertical main axis, respectively, in the range of 40-50°, very preferably an angle in the region of 45° or of precisely 45°. If there are two such additional axes, they can be perpendicular to one another, i.e., they enclose an angle of 90° with one another, but it is also possible that the diagonal main axes enclose an angle in the range of 20-160° with one another, for example in the range of 60-120°. The diagonal main axes preferably enclose an angle of 80-100° with one another, in particular an angle in the region of 90° or of precisely 90°. Actuation of the electronic device: This actuation, either to transfer into a next individual measurement or to displace the alignment mark, can be performed either directly on the display screen (for example, upon use of a touch-sensitive display screen) or else it is possible to provide an additional input interface. Via this interface, for example, movement information of the user (nodding of the head or other body part movements) can also be registered, either a central unit or a special device for actuation can be provided for the registration, for example, in the case of data spectacles, the movement of the alignment mark can be controlled by movement of the head, by speech input, or by corresponding manual input on the data spectacles.

Since the vision system is trained to always focus on the point which is to be assessed, for the test subject in the scope of the classical determination of the Vernier acuity via the Amsler grid, it is almost impossible to fulfill this task without turning the fixation away from the requested fixation point. However, the examination thus becomes worthless. The advantage of the test method described here is that the studied subject has to focus on the point which he has to displace. This corresponds to the normal physiological vision procedure, in that one is able to turn ones visual attention to the point which has to be manipulated. Since the studied subject aligns the point to be manipulated in relation to the two outer points which are also displayed, the effectively tested points are these two outer points. This measuring procedure thus enables the measurement of points outside the central point of focus, without the studied subject intentionally having to concentrate on points outside the point of focus.

By way of a dynamic adaptation of the test imaging to the effective test conditions (spacing of eye from image or rotation of the head or the screen), the quality and reliability of the measurements are increased. By way of the additional registration and analysis of the required chronological duration of the partial tasks until the user has subjectively positioned the alignment mark optimally on the connecting straight line, and also by way of the registration and analysis of the number and size of the control movements per partial task, the static examination of the Vernier function is expanded by a dynamic component, whereby the sensitivity threshold for the discovery of degenerative or also pathological changes can be lowered. The method additionally enables a continuous adaptation of the test and the display to the capacities and needs of each individual eye of a user.

According to a further preferred embodiment, the present invention moreover relates to such a method, which is furthermore characterized in that in the scope of one test series, at least two or at least three test procedures are carried out along the vertical main axis and two or at least three test procedures are carried out along the horizontal main axis. It is alternatively or additionally possible to carry out at least two or at least three test procedures along each of the two diagonal main axes.

With reference to these diagonal main axes, it is not to be strictly understood that these inclined main axes have to be at an angle of 45° in relation to the vertical or horizontal main axis, respectively. What is essential is that these diagonal main axes have a deviation from the vertical and the horizontal main axis sufficient for these applications. These diagonal main axes typically enclose, preferably independently of one another, an angle with the horizontal or vertical main axis, respectively, of 10-80°, preferably in the range of 20-70°, particularly preferably in the range of 30-60°. These diagonal main axes very preferably enclose an angle with the horizontal or vertical main axis, respectively, in the range of 40-50°, very preferably an angle in the region of 45° or of precisely 45°.

The two diagonal main axes are preferably perpendicular to one another, i.e., they enclose an angle of 90° with one another, but it is also possible that the diagonal main axes enclose an angle in the range of 20-160° with one another, preferably in the range of 60-120°. The diagonal main axes preferably enclose an angle of 80-100° with one another, in particular an angle in the region of 90° or of precisely 90°.

The arrangement of the test points on various axes enables the testing of various, precisely defined points of the retina. This enables degenerative processes which exist from birth or processes which are pathological to be associated with certain areas and points of the retina. In fact, the entire region of the macula can thus be studied in detail. The measuring range extends over at least a circle of a radius of 10° about the fixation point. Since, according to the proposed method, the measured points can be measured very accurately and reproducibly, this association is very accurate, in contrast to other methods, for example the Amsler grid, which only permits this association imprecisely. It is specifically possible by way of appropriate skillful control of the measurement or the selected starting locations along the various main axes, respectively, to effectively determine the weaker regions on the retina for each eye by targeted data analysis. Areas can thus be identified on the retina by the different measurements along various axes and with various spacings of the alignment mark from the outer marks, wherein these areas are typically circular segments or, as a result of the various spacings of the alignment mark from the outer mark, even circular ring segments. A mapping on a polar grid, as it were, can thus be performed, wherein the various grid areas can be assessed individually.

As described above, various parameters can be used as the measure for determining the visual acuity of the user. According to a further preferred embodiment, in the case of registration of the parameter of the effective spacing of the alignment mark from the connecting straight line after displacement of the alignment mark by the user as the measure for determining the visual acuity, the mean value and/or the standard deviation of the absolute value of the effective spacing of the test procedures along the same main axis is used.

If, additionally or alternatively, a registration is performed of the parameter of the time which the user has required for the displacement of the alignment mark, and this is evaluated as a measure for the determination of the visual acuity, the mean value and/or the standard deviation of the total time between the appearance of the marks and the confirmation of the end of the individual test procedure can be used. If, as the end of the individual test procedure, for example, the next measuring procedure is proceeded to automatically upon a lack of input within a certain number of seconds, it is also possible to take that point in time as the end at which the last manipulation has taken place.

If, additionally or alternatively, a registration of the number of direction changes during the displacement of the alignment mark by the user is registered as a parameter, the mean value and/or the standard deviation of the number of direction changes during the individual test procedures can be used, or the total of the direction changes along a certain main axis. Under this parameter, the amplitude and/or the frequency of such direction changes can additionally also be registered and analyzed.

In addition to the parameters specifically mentioned here, still further parameters can also be registered and incorporated into the data analysis for determining the visual acuity. These include, for example, items of information which are recorded via the camera oriented toward the user and, for example, items of information about the eye, the activity of the eye during the measurement, etc. The position of device relative to the user, and the movement of the device (via corresponding gyro elements/sensors), and items of information about the brightness of the surroundings, the time of day, the time since the last examination, etc. can also be incorporated.

Since the Vernier acuity varies depending on various physiological influencing factors, for example time of day, learning effect, and alignment of the tested axis, these influencing factors are supplemented by additional analysis of the dynamic test parameters such as required duration for the partial tasks and number and size of the required control and correction movements. This enables better differentiation between changes of the measurement results which are related to visual capacity and form on the day or are induced by learning effects. Thus, insofar as the method is used to measure retina-related influences on the visual acuity, non-retina-related influences on the measurement accuracy can be filtered out or weighted correctly, and the sensitivity of the method for the determination of changes related to visual acuity can thus be increased. On the other hand, specifically these further parameters, if the method intends generally to measure the perception capacity of the user, for example (in the context of an alcohol test, for example), can be taken into account as relevant additional parameters in the analysis. These further parameters can thus be used both for further refinement of the measurement results, and also to prevent the corruption of the measurement results.

According to a further preferred embodiment, the method is characterized in that test procedures are begun along the same main axis with different offset of the alignment mark in each case along the connecting straight line, wherein preferably an offset of ⅓, ½, and ⅔ of the distance between the two outer marks is specified along each main axis at the beginning of the respective test procedure. The number of the individual test procedures and/or the respective offset can preferably be adapted individually in this case on the basis of prior examination results or preceding morphological examinations. Due to this different relative position of the alignment mark in relation to the outer marks, it is possible to measure not only circular sectors on the retina or the field of vision, respectively, but rather circular ring sectors.

The test method permits the examination of a very large area of the retina. Degenerative, pathological, or other processes are often restricted to narrowly circumscribed regions of the retina, however. Affected regions may be found rapidly in the context of a search function by means of the offset of the points selected at the beginning, and may be more closely delimited in the further course of the measurement by selection of the location of the measurement points. This is because in actual fact it is possible to specifically adapt future test series depending on measurement results of previous test series, or to reduce them to the decisive measurements, respectively. By way of the reduction of the number of individual test measurements, the accuracy thereof can also be substantially increased, since symptoms of fatigue of the user should have a lower influence.

According to a further preferred embodiment, the outer marks and the alignment mark can be strokes or circles having a length or diameter, respectively, in the range of 1-10 mm, preferably in the range of 2-4 mm. In the case of strokes, they can be strokes having a stroke thickness in the range of 0.5-5 mm, preferably in the range of 1-2.5 mm. In this case, all strokes are preferably aligned parallel to the main axis to be measured during the entire test procedure. The size of the outer marks and the alignment mark can be equal, and they can be adapted in the size thereof to the visual acuity of the test person.

According to a further preferred embodiment, at least one of the following setting parameters is individually adapted on the basis of prior test series and/or prior individual test procedures and/or preceding morphological examinations: the size of the marks; the contrast on the display screen; the color selection on the display screen; optionally additionally provided focusing aids, wherein this individualization is preferably performed for each specific eye of the user.

The user preferably carries out the test series using only one eye and/or the electronic device ensures that the information displayed on the display screen can be perceived by only one eye.

The method can thus be individualized both for each eye and each user. Accordingly, depending on measurement results, the shape and size of the marks, the contrast, or possible focusing aids can be individualized for each eye and displayed for each input during the measuring procedure.

The smaller the measuring marks are selected to be, the more precisely may the vision quality Vernier acuity be determined. The recognition of the test marks is dependent on the vision quality or visual acuity, however. The worse the visual acuity, the larger both the alignment mark and the outer marks have to be so that they can be recognized by the examined person. In the present test, the size, type, and contrast of the test mark can therefore optionally be adapted to the visual acuity of the person to be tested. The vision quality Vernier acuity can thus still be reliably tested in particular in test persons having greatly reduced visual acuity. This differentiates this test significantly from other methods for testing the Vernier acuity, for example the Amsler grid, where the test patterns have a constant size. If the visual acuity of the eye to be examined is reduced so much that the test person has difficulty in consistently maintaining the fixation on the outer marks, additional focusing aids can be overlaid, for example a ring display located outside the test marks around the entire test field.

A further preferred method is characterized in that the user controls the displacement of the alignment mark by a direct or indirect interaction with the electronic device, wherein this interaction can be performed by means of a touch-sensitive display screen, body movements, in particular of the hand or the head, or by speech, or a specific input interface, for example a manual input device or else via an input device coupled on via Bluetooth (for example, if the display screen is produced via a projection), or a combination thereof, wherein, if the display screen is a touch-sensitive display screen, the user either aligns the alignment mark directly by touching and displacing the alignment mark on the display screen, or does so with the aid of one or more displacement knobs which are depicted on the display screen. The type, size, number, direction, and the time requirement for the interaction of the user with the input aids for guiding the test mark into the target region can also be measured and used for the improvement of the measurement sensitivity and also for the assessment of the form on the day of the user or of the learning effect.

Since older persons offer suffer from changes of the retina, the interaction with the measuring device can be made more difficult. These difficulties may be avoided by way of the manifold options for interaction possible according to the present invention. The interactions, using which the test is controlled, correspond to typical everyday interaction patterns, in that an interaction is able to be performed using gestures or head movements such as nodding the head or shaking the head.

As already described, it is possible, by measuring the time until correct positioning of the test mark is achieved, to indirectly determine a change of the visual function, in addition to the actual Vernier acuity measurement. Even very slight worsening of the visual function results in an increased time requirement for the correct positioning of the test mark. Indications of worsening of the vision function in a certain retinal area exist if the time for solving the partial task on a certain axis or a point becomes longer in comparison to earlier examinations, or if the difference between the slowly and the rapidly solved partial tasks increases in comparison to earlier examinations. If an increased time requirement for solving the task is established on one or more test axes (required time lies outside two standard deviations, for example, of the time required for these test points in earlier examinations), the device will propose a shortened interval until the next testing (for example, 3 instead of 7 days). If progressive slowing over multiple measuring days is established, additional measures, for example a request to visit an optician or physician, or further measures are recommended. If the method determines that the time requirement for all tasks increases or decreases, this is an indication of generally better or worse vision function, a varying form on the day of the user, or a learning effect. This information can be used to adapt the size of the test marks in the case of an unambiguous trend, or to weight the results differently with respect to the use in the individual database (baseline for the normal test result of an axis or an area). This can prevent examination results of test checks on generally poor days for the user or the effect of the learning curve from causing the statistical reference value for an expected performance of the user on an axis to become incorrectly low. The sensitivity of the method thus remains consistently high in spite of learning curve or changed test displays.

The method offers the option, in contrast to the previous measuring methods with analysis of solely static measured variables of the Vernier vision function, by way of the measurement of a dynamic component, of substantially increasing the sensitivity for the discovery of a change of the Vernier vision function and also of taking into consideration and compensating for effects such as form on the day, learning curve, or changed display.

A measurement of the required number of correction movements, which is also possible as already described above, and also of the size and/or amplitude of the overshooting correction movements until the definitive positioning of the test mark, can be registered. An increased number of correction movements or an increase in the amplitude of the correction movements on one axis or multiple axes in comparison to the values determined in the preceding examination cycles is an indication of a local worsening of the Vernier vision function. Indications of worsening of the vision function in a certain retinal area exist if the number of correction movements for solving the partial task on a certain axis or a point increases in comparison to earlier examinations, or if the difference between the most and least successfully solved partial tasks increases in comparison to earlier examinations. Similarly to a measured worsening of the chronological component of the Vernier vision function test, in the event of worsening of the number or the amplitude of the dynamic components of the Vernier vision function test, the method will recommend a reduced interval until the next test or additional measures.

The advantage of this second component of the dynamic test of the Vernier vision function also enables increased sensitivity of the Vernier vision function test for the early determination of very slight worsening of the vision function. Moreover, influencing variables, such as the form on the day or learning effects, of changes related to visual capacity can be differentiated better, since form on the day and learning effect influence the number and size of the correction movements for all partial tasks, axes, and retinal areas, while pathological changes predominantly occur in the region of already diseased retinal areas or only individual areas having worse function.

A measurement of the required number of correction movements and the size (amplitude) of the overshooting correction movements until the definitive positioning of the test mark can be performed in consideration of the static results of the Vernier vision function test (spacing of the mark from the axis). If a strong and general increase of the required number and amplitude of the performed correction movements (dynamic component) on all axes is determined without worsening of the static test component (increase of the effective spacing of the alignment mark from the connecting straight line), then this is an indication of a change of the form on the day of the test person or an effect of the learning curve or an effect of the changed test display or is caused by a general slowing of the central nervous system performance and control of the coordination, for example as a result of sedative, hallucinogenic, or intoxicating substances such as alcohol. In this case, the results of this measurement of the Vernier vision function are not considered or are only considered in a reduced form for the determination of the individual reference values of the long-term vision function of the test person. This can prevent examination results of test checks on generally poor days for the user or the effect of the learning curve from causing the statistical reference value for an expected performance of the user on an axis to become incorrectly low. The sensitivity of the method thus remains consistently high in spite of learning curve or changed test displays. In the event of a suddenly occurring, substantial deviation from the typical form on the day (more than 2 standard deviations), the method will recommend to the test person to take measures or temporarily stop activities (for example driving vehicles and using hazardous machines).

The advantage of the combined dynamic and static analysis of the Vernier function is that, in addition to a visual component, the response capacity of the test person can also be measured. Short-term worsening as a result of the fluctuating form on the day of the test persons (fatigue, time of day, sedative substances) can thus be partially or even completely differentiated from retina-related worsening. Worsening caused by the present form on the day can thus be statistically underweighted with respect to the long-term analysis in relation to the solely retina-related worsening of the vision function. By filtering out the noise in the Vernier vision function caused by the form on the day, the sensitivity of the test to the solely retina-related changes of the Vernier vision function is increased once again.

A further preferred embodiment of the proposed method is characterized in that a qualitative analysis or a quantitative analysis is output on the display screen as a function of the determined visual acuity, or a notification that medical aid should be sought.

According to another preferred embodiment, the arrangement of the outer marks and the alignment mark is individually adapted for the various individual test procedures on the basis of the statistical analysis of the preceding measurements.

In contrast to other measurement methods, the present test permits a quantitative measurement of the Vernier acuity of individual retinal areas. The measurement results of the individual test points are less informative taken per se with regard to the dynamics of a pathological procedure and are not interpretable by a user of the test. However, by way of statistical methods in consideration of preceding measurements or other measurement points registered in the same examination, the dynamics of a pathological or degenerative process may be derived. Only this information and not the results of individual measurement points is significant for the user and is directly provided to the user.

The data ascertained in a test series, optionally in combination with items of information about the user, in personalized or anonymized form, can moreover be transmitted to a central office according to a further preferred embodiment, preferably via an Internet or mobile telephone connection, and at this central office, the data can be stored, further processed, and/or relayed for information and/or further processing to medical support.

The electronic device can additionally have sensors (including a camera oriented toward the user, movement sensors/acceleration sensors, orientation sensors, optical or thermal sensors, sound or odor sensors), and can thus determine the behavior of the user, in particular the spacing of the user from the display screen, and/or the eye spacing, and/or whether the test procedure is carried out in a monocular or binocular manner, and in the first case, which eye is closed in this case, and/or the rotation of the display screen about the vision axis and/or the orthogonality of the vision axis to the surface of the display screen. This information may be incorporated into the data analysis and/or a notification may be transmitted via the display screen or acoustic signals or speech output to the user to set the corresponding variable to the correct value. Additionally or alternatively, it is possible to use this information to carry out and record the measurement optimally. Thus, the display occurring on the display screen of outer marks and alignment mark can advantageously be adapted, preferably even dynamically adapted within one test procedure or between the test procedures of one series, on the basis of these items of information. The camera or other sensors of the electronic device can additionally be used for the unambiguous identification of a test person or of the behavior thereof during the measuring procedure or also before or after, respectively, the measuring procedure (for example, via facial recognition, fingerprint, or voice recognition). The location or size of the test marks on the display screen can also be adapted dynamically during the test procedure, in particular depending on the measured effective distance and the rotation of the display screen, such that the projection of the measurement points on the retina remains consistent. Measuring methods for determining the Vernier acuity can only supply reproducible and quantifiable results if it is ensured that identical points on the retina can be measured repetitively. The present invention adapts itself to the user dynamically in this regard by means of sensors.

The electronic device is preferably a portable device, in particular a personal digital assistant (PDA), smartphone, mobile telephone, tablet, laptop, smart watch, data spectacles, or head-mounted display. In this case, the method can be based on a two-dimensional or three-dimensional depiction. The testing of the Vernier vision function can be performed in a monocular or binocular manner. Binocular testing results in a reduced time requirement for the testing of both eyes. The time savings can be used if needed for measuring additional areas or for additional measurements on critical areas.

The results of various successively carried out test series, preferably test series carried out on different days, can be evaluated relative to one another in the development thereof by the electronic device and the development of the visual acuity can be determined, and preferably upon reaching a threshold value of a variable computed from the test series, a warning can be output to the user and/or can be transmitted via an interface to a central office for making contact with the user.

The checking of the dynamics of the visual acuity is decisive for the detection and monitoring of pathological processes. Individual measurements taken per se only have limited informative power. The evaluation within the course increases the informative power significantly and also allows other, non-pathological variations of the vision function, which are not of interest, to be filtered out. By filtering out the non-pathological variations of the vision function, the accuracy and sensitivity of the method for determining pathological changes can be significantly increased in relation to previous methods for determining the Vernier vision function. According to a further preferred embodiment of the method proposed here, the electronic device can prompt the user, in the scope of a specified time plan, to carry out a test series in each case at a certain point in time, wherein preferably, depending on the result of a preceding test series and in particular depending on changes of the results of the immediately preceding test series in relation to the base value determined by multiple preceding test series, a renewed test series is recommended to the user in the scope of a fixed time scheme, for example every 3-14 days, or preferably every 7 days, or, in the event of established worsening of the results, after only an individually shortened time interval.

Carrying out vision tests can represent a significant burden for the examined persons and can therefore have the result that the tests are no longer carried out or are no longer carried out with sufficient and suitable attentiveness. Since many retinal diseases are of a chronic nature, testing over long periods of time is necessary. The frequency of the test procedures therefore occurs in the present test not according to a fixed time scheme, but rather is individually adapted based on previous measurement results and other factors. In addition, specifically the sequence of the individual measurements can also be focused in a very targeted manner on the problem zones, namely only those main axes are measured which are actually relevant for the corresponding user. The control of the time intervals can also be performed individually only for the eye having a change of the results (for example, in the event of worsening of the left eye, only the recommended examination interval of the left eye is shortened). Due to the individual control of the time intervals until the next check, the time burden on the user can be minimized. Moreover, additional measurements or test axes for improved measurement accuracy or test sensitivity can be added to an eye having worsening, while only a short basic check has to be carried out on a stable eye. Moreover, the test person is prompted to perform the testing in each case.

As already mentioned, according to a further preferred embodiment, the measurement data of the electronic device can be transmitted to a central computer and analyzed therein using algorithms. Possible algorithms are, for example, the determination of i) the variance increase of the measurement point spacings relative to a comparative measurement;

ii) the consideration of patient characteristics, such as in particular age, sex, ophthalmological findings such as eyesight, eye diseases, and systemic diseases;

iii) subjectively experienced degree of difficulty of carrying out the test, test duration, amount and amplitude of the control and correction of the test mark and the progression of the test results, and any possible therapeutic measures.

The results of such analyses can be processed as personalized feedback, preferably individualized each eye, and provided to the user, and the results can be used to individualize the measuring arrangement, wherein this individualization can consist in a change of the measurement axes, the measurement points, the measurement interval, and the assessment of the measured values. The testing is preferably performed with a covered eye. The test can also be carried out with both eyes simultaneously, wherein depending on the test results, a prompt can then be made to carry it out with a covered eye.

Furthermore, the present invention relates to a portable electronic device for carrying out a method as was described above, having a display screen and a data analysis unit, wherein the display screen is preferably a touch-sensitive display screen, and wherein furthermore the electronic device preferably additionally has a camera oriented toward the user. The display of the test tasks can be performed two-dimensionally or three-dimensionally depending on the capability of the device used.

Finally, the present invention relates to a data processing program for carrying out a method as described above on a device as described above, preferably in the form of a mobile application (app).

Further embodiments are specified in the dependent claims.

BRIEF DESCRIPTION OF THE DRAWINGS

Preferred embodiments of the invention will be described hereafter on the basis of the drawings, which are only used for explanation and are not to be interpreted as restrictive. In the figures.

DESCRIPTION OF PREFERRED EMBODIMENTS

Figure 1A:
FIGS. 1 a) and 1 b) show in FIG. 1 a) a user of the proposed method, who holds a mobile device at the proposed spacing of approximately 30 cm in front of her eyes, and in FIG. 1 b) a graphic representation of the relative arrangement of outer marks arranged along a horizontal main axis and an alignment mark and the corresponding distances and spacings and also designations for the situation, where the offset is approximately ⅔.
Figure 1B:
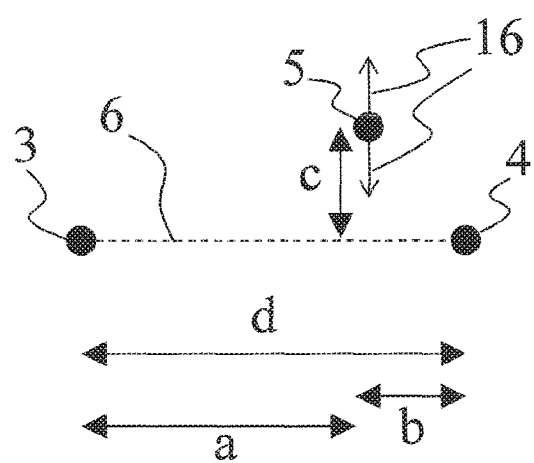

FIGS. 1 a)-b) show a user, who holds a smartphone 2, which has a touch-sensitive display screen 1, in front of her eyes. Software in the form of a mobile application (app), which implements the proposed method, is loaded on this smartphone 2. It is to be noted in this case that the vision axis is aligned substantially perpendicularly in relation to the surface of the display screen 1, and the longitudinal axis of the display screen is aligned approximately perpendicularly in relation to the connecting line of the eyes, in any case the rotation of the display screen relative to the face of the user should not be changed within one test series.

In order that a correct alignment of the smartphone is indicated to the user, it is possible to also incorporate the camera and optionally further sensors (for example gyroscope and accelerometer) of the smartphone into the software, and after starting the software, initially to determine via the camera or other sensors, respectively, for example, via a corresponding facial recognition of an image of the user recorded by the camera, whether a correct relative position of display screen to the user is assumed, and if necessary to cause optimum positioning by way of corresponding warning notifications or even by way of concrete modification instructions (for example, "the display screen is located 2 cm too close to your eyes, please hold farther away," or "the monitor is tilted in relation to the head direction—please rotate 5° clockwise," or by overlaying an auxiliary axis), which can be output either visually, in written form, or also acoustically. The incorrect alignment of the display screen in relation to the eyes or deviations of the test distance can be compensated for continuously and automatically if necessary by dynamically changing the location of the points on the display screen during the test sequence, or it is possible to correct the registered parameters depending on such deviations, so that the deviations from the correct hold have no influence on the measurement result. Moreover, via the facial recognition, the person can be identified the measured side (left or right eye), monocular measurement, and other parameters influencing the quality of the measurement can be remedied and the display or the algorithm of the test sequence can be adapted to the individual visual capacities of the left or right eye, respectively, of a test person or corrected.

Using such sensors (movement sensors/acceleration sensors, orientation sensors, etc.), it is possible to monitor the general behavior of the person who carries out the test, presuming that the person always carries the measuring device with him. In other words, the measuring device can simultaneously also be used as an activity tracker, and the data determined therefrom can be incorporated into the analysis of the test procedures described here. Thus, for example, from general activity of the user which remains uniform per se before and after the measuring procedure, it can be concluded that although the measurement results were perhaps somewhat worse, the activity has remained the same, in contrast, and apparently the worse measurement results do not mean life-changing impairment of the vision behavior. The activity of the user can also be detected via separate sensors fastened on the body (for example armband, activity tracker) and transmitted directly or indirectly to the device and/or to a central office, which then takes this activity into consideration in the analysis of the data transmitted from the device to the central office.

Figure 2A:
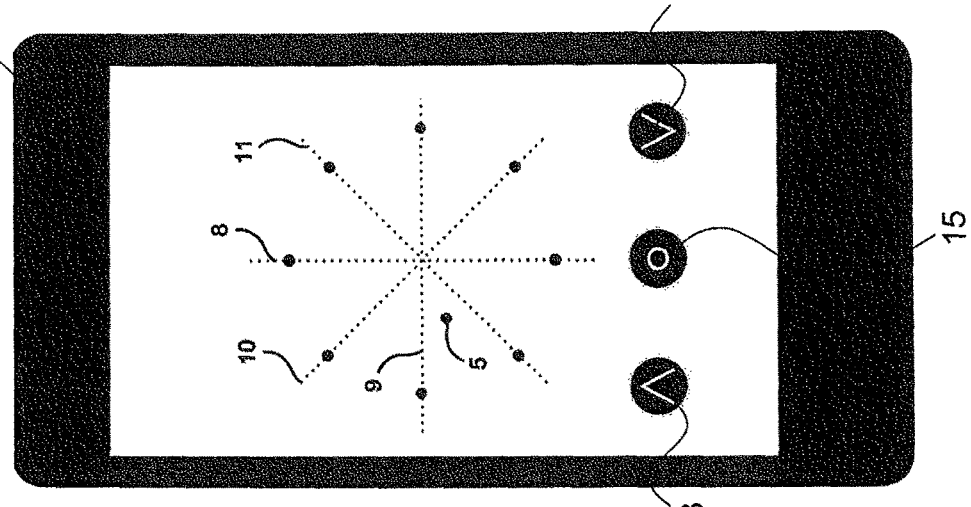
FIGS. 2 a)-2 d) show the different displays in the proposed method, wherein in FIG. 2 a) the starting situation of an individual test procedure is shown, in which the outer marks are arranged horizontally, in FIG. 2 b) the location of the alignment mark after manipulation by the user is shown, in FIG. 2 c) the various main axes are shown simultaneously, and in FIG. 2 d) the region for the offset is schematically indicated for the situation where the outer marks are arranged horizontally.
Figure 2B:
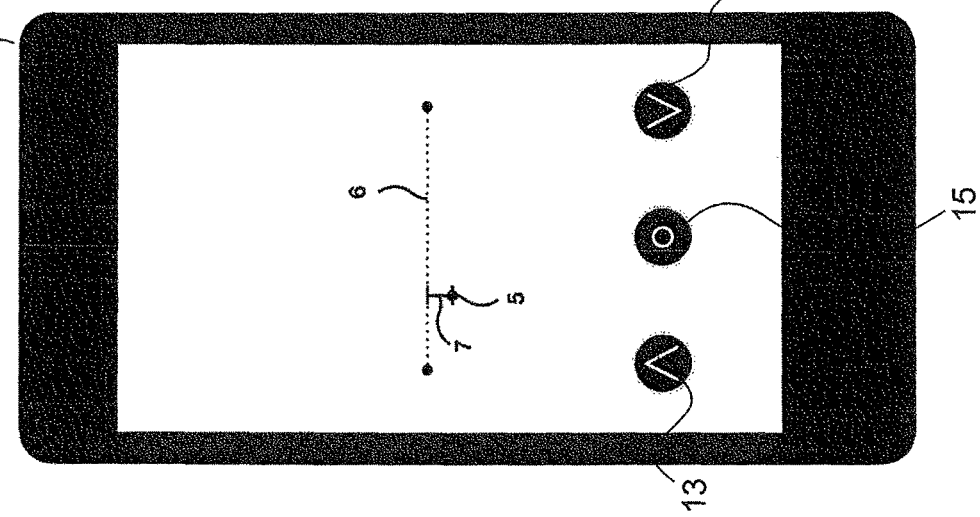

The starting location in a first individual test procedure is shown in FIG. 2a. In this case, the main axis 6 is arranged horizontally, i.e., the two outer marks 3 and 4 are displayed at approximately half the height on the display screen at the right and left edge, respectively, and the connecting straight line 6 extends horizontally.

It is to be noted in this case that in the effective test, the connecting straight line 6 shown by dotted lines in each case here in FIGS. 2 a)-2b) is of course not made visible, but rather is specifically omitted, so that the user concentrating on the alignment mark 5 is forced to orient himself to a certain extent by regions which are not in focus and are defined by the two outer marks 3 and 4 and therefore to use the regions to be measured accurately.

As the starting situation, the alignment mark 5 arranged more or less between the two outer marks 3 and 4 is displaced substantially downward in this case and arranged somewhat to the left of the center between the two outer marks 3 and 4.

There are now three touch-sensitive regions on the display screen 1 in the lower region. A first region 13 is indicated on the outside at the far left, which, upon being touched by the finger, displaces the alignment mark 5 upward, i.e., in this case closer to the connecting straight line 6 and perpendicularly thereto. A second region 14 is indicated on the outside at the far right, using which the alignment mark can be displaced in the opposite direction, also perpendicularly to the connecting straight line. These two regions 13 and 14 are always provided so that the alignment mark can only be displaced in one direction or in the opposite direction, respectively, perpendicularly to the connecting straight line. The arrows shown on the regions 13 and 14, respectively, rotate accordingly, so that the user can recognize which function or which direction, respectively, relative to the connecting straight line is associated with which knob.

Moreover, a further touch-sensitive region is located in the middle, using which the individual test procedure can be completed and the series can proceed to the next.

The various touch-sensitive regions 13-15 can also be arranged in other regions of the overall display screen, of course.

Furthermore, it is to be noted that instead of the regions 13 and 14, respectively, a procedure can also be used in which the positioning of the alignment mark 5 can be performed directly by laying a finger on the touch-sensitive display screen and displacing the finger appropriately.

Proceeding from the starting situation shown in FIG. 2a, the user will now displace the alignment mark by the actuation of the regions 13 and 14, respectively, until he subjectively has the feeling that it is located on the connecting straight line 6 (which is specifically not shown in the effective experiment, although it is shown in FIG. 2 to facilitate the description). If the user is of the opinion that the alignment mark 5 is located on the connecting straight line 6, for example in the position as shown in FIG. 2b, he can progress to the next individual test procedure by way of the central region 15. When he does this, the spacing 7 of the alignment mark 5 from the connecting straight line 6 is read out and stored by the software. This spacing 7, as described in greater detail hereafter, is used for the analysis. In addition, the required time until the test person has subjectively correctly aligned the mark, and the number and amplitude of required direction corrections during the displacement of the mark, can also be registered and subsequently analyzed for the analysis.

Figure 2C:
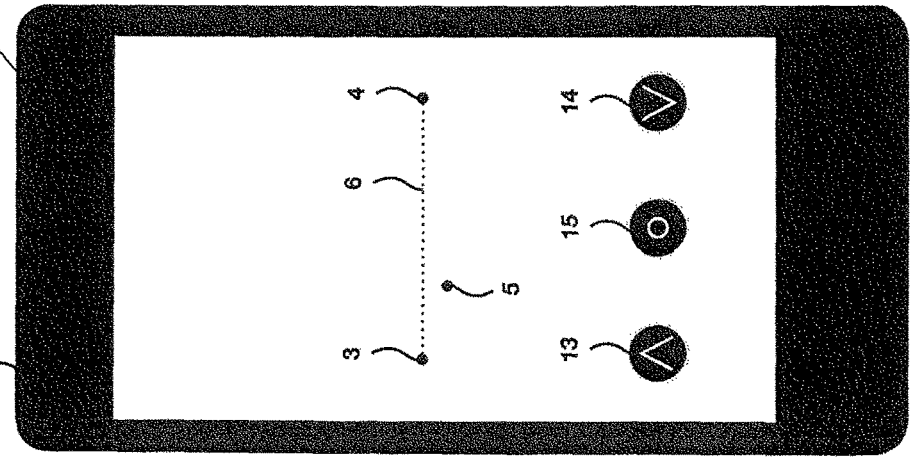

Various such individual test procedures are now carried out in a manner which appears random to the user, wherein in each case at least three test procedures are carried out along one main axis (cf. description of FIG. 2c).

The various main axes measured in this case are shown in FIG. 2c. On the one hand, the horizontal main axis 9, as is also illustrated in the individual test procedure according to FIGS. 2a and b, then the vertical main axis 8, and also a first diagonal main axis 10 and a second diagonal main axis 11.

If all main axes are measured and three measurements are performed on each main axis, this results in 12 measurements, which can sometimes also be perceived as burdensome. To keep the number of actually useful measurements as low as possible or to represent slight changes better and earlier by way of focal point measurements at the edge of the diseased retinal areas, it is possible by transmitting the measured data of a test series to a central computer in each case to compare the individual test procedures to earlier test results and adapt them for later measurement series to those areas which were actually previously found to be problematic. For example, if a user has a weakness which is manifested by the measurements on the second diagonal main axis, but no problems on the first diagonal main axis, it is thus possible for the first diagonal main axis not to be measured during each test series or for only individual measurements and no longer multiple measurements still to be performed per axis. The analysis of the results and adaptation of the test sequence are preferably performed individually for each tested eye.

Figure 3:
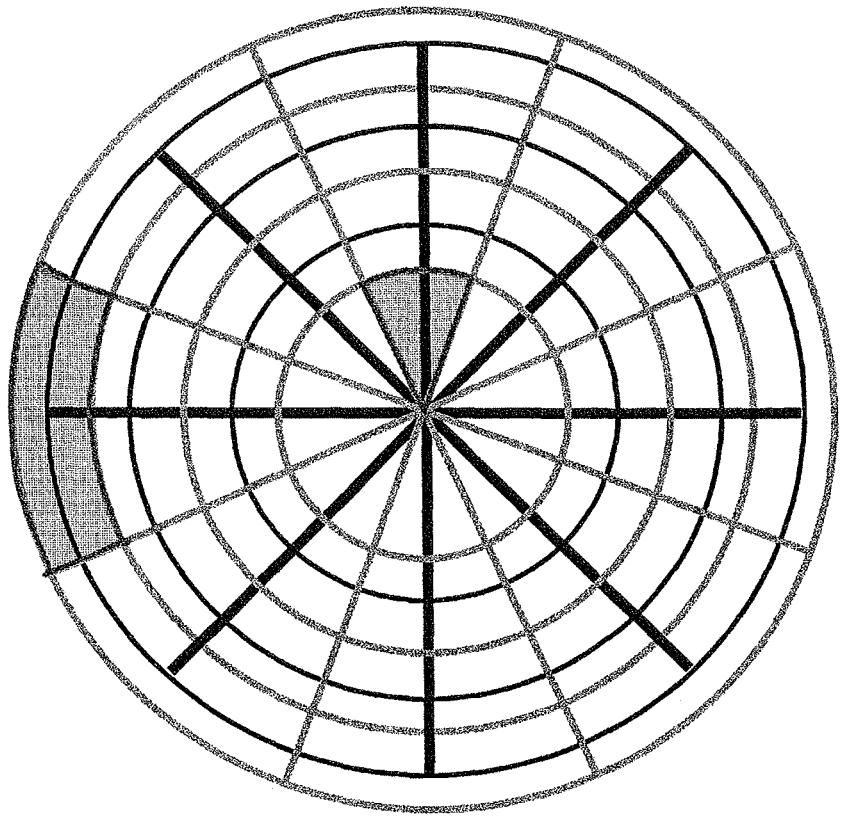
FIG. 3 shows possible topographic results of the measurement in a polar grid, wherein the measurement axes are shown in black: these form the center lines of retinal sectors, the delimitations of which are shown in gray; the gray areas mark affected retinal sectors; the system can be adapted, made more precise, and optimized in a self-learning manner on the basis of the analysis of affected sectors on the basis of the testing in the edge regions.
Figure 2D:
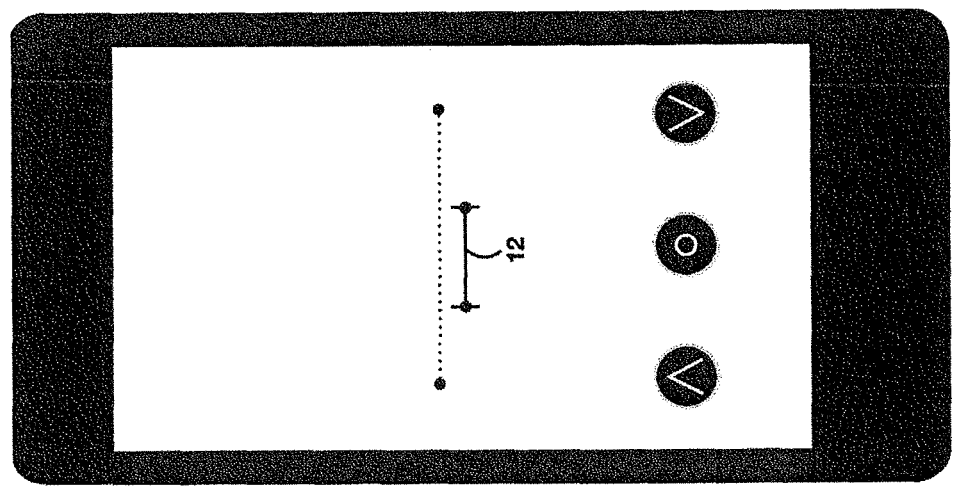

As described above, the alignment marks are presented during the individual test procedures in different positions relative to the two outer marks in the starting situation. The offset 12 which is reasonably possible in this case is illustrated in FIG. 2d. This offset typically moves between either the center or between ⅓ and ⅔ of the distance between the two outer marks 3, 4. To make a measurement result more precise, to prepare a retina mapping (FIG. 3), to determine the field of vision or as a reaction to pronounced vision restrictions of an eye, the test procedure can be displayed in an individualized form for each eye with respect to the shape and size of the outer marks, the spacings thereof, the contrast, possible additional focusing aids, or other measures, such as color change.

For the analysis of the actual test procedures within the test series, the spacings 7 which the alignment mark 5 has in each case at the point in time when the user changes to the next individual test procedure (cf. FIG. 2b) are now collected and statistically analyzed. In this case, for example, a procedure can be used such that the mean value of the absolute value of the measurements along a certain axis is used, and also the scattering thereof. Subsequently, mean value and scattering in relation to each of the 4 axes can be output as a measurement result. Further parameters gathered during the measurement, for example, the duration of the entire examination or the duration until the positioning of individual points, and also the number and size or amplitude of the correction movements and/or the changes of these parameters upon repeated measurements, can additionally be used to improve the measurement or to reduce the detection threshold for pathological changes. Furthermore, it is possible that the damaged areas are identified along each main axis and fine mapping of the corresponding retinal section can be completed there. The spacings of the outer marks for individual axes can be adapted in conjunction with the retinal mapping.

The measurement result can either be generated autonomously on the smartphone itself, or else a procedure can also be used in which the raw information (individual measurement points) is transferred to a central server, the analysis takes place therein, in particular also depending on already completed test series, and feedback occurs after central analysis.

In the case of communication with a central computer, it is also possible to have corresponding feedback be sent not only to the user, but rather also, for example, to an optician or medical personnel.

The feedback can, on the one hand, consist of statistical analysis with numbers or, on the other hand, be performed in a more detailed form, for example with the prompt to visit an optician or medical personnel, to take further measures, or to stop activities, for example driving vehicles or operating hazardous machines.

It is possible, for example, to prompt the user initially or in each case at defined intervals to carry out an initialization measurement series, which more or less determines a baseline of the individual capacities. A variation range which is characteristic for the corresponding user is determined from these initialization measurements, preferably individually for each measured axis. This means that upon measurement of the horizontal and the vertical axis and also the two diagonal axes, four variation ranges are determined in these initialization measurements, one for each axis. This means that along each axis, the obtained measured values in this initialization measurement are subjected to a statistical analysis individually for each axis, and an individual variation range is then established for the respective axis. This is preferably performed such that twice the standard deviation of the spacing of the alignment mark from the connecting straight line is used as the variation range.

Direct and helpful feedback, which is useful for the user, via the display screen can then be embodied independently of the further statistical analysis of the measurements in the background so that when all 4 axes have been measured in the respective performance of the test series, for each individual test procedure in which the user aligns the alignment mark within the defined variation range (specifically, for example, within the range+/−standard deviation as determined from the initialization measurement series, wherein this standard deviation can be adapted successively proceeding from values determined in an initialization measurement series in the course of regular continuation the test series over a relatively long period of time), a point is awarded. If 3 measurements are carried out per axis along the 4 axes, a maximum of 12 points per test series thus results. After completion of the test series, the number of achieved points can be output via the display screen, and backed with additional optical feedback. Thus, for example, the deviation from the maximum number of points can be indicated as a measure of the quality of the test series, and upon reaching 11 or 12 points, a value of 0 or 1, respectively, can be output, backed with green, in the sense of everything in order, no further action required, upon reaching 9 or 10 points, a value of 2 or 3, respectively, can be output, backed with orange, in the sense of caution, the development is not advantageous, and upon reaching less than 9 points, the corresponding difference value can be output, backed with red in each case in the sense of caution, action required, please contact the physician. The corresponding scale and/or at which number of points which warning, is output visually or supplemented by additional messages, also optionally via the audio output, can also be set individually depending on the medical situation, age, and preference of the user.

The test is preferably carried out with only one eye. With devices in the case of which both eyes can see the same image display simultaneously (for example smartphone, tablet computer, and the like), the other eye is preferably covered or closed. If an eyepatch is used for covering, patterns, characters, or machine-readable codes (for example QR code) can be applied thereon, which the camera can register and thus can obtain data (for example on the test person). A binocular performance of the test is also possible with the above-mentioned devices, wherein the worsening of the vision function can initially not reliably be associated with a certain eye. If a change of the vision function is noticed during the binocular examination, the examined person can be requested to carry out monocular tests. The eye which must be tested is determined on the basis of the results of the preceding examinations and/or the progression thereof. In the case of screens having the option of a three-dimensional (spatial) display, by using an additional offset of the test mark in the third dimension, the test accuracy of a binocular test can be improved. When carrying out the test with data spectacles or devices which display a three-dimensional or virtual reality or can present a different image to each eye, covering the contralateral eye can also be omitted in the case of monocular testing.

| LIST OF REFERENCE NUMERALS | |
|---|---|
| 1 | display screen |
| 2 | electronic device, mobile telephone, smartphone, smart watch, data spectacles |
| 3 | outer mark |
| 4 | outer mark |
| 5 | alignment mark |
| 6 | connecting straight line |
| 7 | effective spacing after manipulation by the user |
| 8 | vertical main axis |
| 9 | horizontal main axis |
| 10 | first diagonal main axis |
| 11 | second diagonal main axis |
| 12 | offset |
| 13 | touch-sensitive region for displacing the alignment mark in a first direction perpendicular to the connecting straight line |
| 14 | touch-sensitive region for displacing the alignment mark in a second direction perpendicular to the connecting straight line |
| 15 | touch-sensitive region for input of the end of the individual test procedure |
| 16 | permitted displacement direction for the alignment mark |
| a | offset |
| b | complementary offset in relation to the total distance d |

LIST OF REFERENCE NUMERALS

| | |
|---|---|
| c | spacing of the alignment mark |
| d | total distance between the outer marks |

The invention claimed is:

1. A method for determining the visual acuity of a user, in which, in the scope of a plurality of individual test procedures carried out in succession and conducted in the manner of a test series,
- in the scope of each individual test procedure, two spaced-apart outer marks, which are fixed within an individual test procedure, and an alignment mark located therebetween but not on a connecting straight line of the outer marks, are displayed to the user on a display screen of an electronic device,
- the user is prompted, by actuating the electronic device, to displace the alignment mark on the display screen exclusively perpendicularly to the connecting straight line of the outer marks until in the perception of the user the alignment mark lies on the connecting straight line, and
- subsequently, after completed displacement of the alignment mark by the user, the electronic device registers at least one of the following parameters:
- the effective spacing of the alignment mark from the connecting straight line after displacement of the alignment mark by the user;
- the time which the user has required for the displacement of the alignment mark; and
- the number of direction changes during the displacement of the alignment mark by the user,
- wherein at least two or at least three individual test procedures are carried out, in which the outer marks are arranged along a same main axis or previously determined auxiliary axes, and wherein the tests are measured with the outer marks arranged along at least two different main axes in the scope of one test series,
- wherein the at least one registered parameter or, upon measurement of multiple parameters, a combination of the registered parameters is used as a measure for determining the visual acuity from the individual test procedures of the test series, and
- wherein in the scope of one test series, at least two test procedures are carried out along a vertical main axis and two test procedures are carried out along a horizontal main axis, and at least two test procedures are carried out in each case along at least one of two diagonal main axes.

2. The method as claimed in claim 1, wherein:
- in the case of registration of the parameter of the effective spacing of the alignment mark from the connecting straight line after displacement of the alignment mark by the user as the measure for determining the visual acuity, at least one of the mean value and the standard deviation of the absolute value of the effective spacing of the test procedures along the same main axis is used; or
- in the case of registration of the parameter of the time which the user has required for the displacement of the alignment mark as the measure for the determination of the visual acuity, the mean value and/or the standard deviation of the total time between the appearance of the marks and the confirmation of the end of the individual test procedure by the user is used; or
- upon registration of the parameter of the number of direction changes during the displacement of the alignment mark by the user, at least one of the mean value and the standard deviation of the number of direction changes during the individual test procedures is used or the total of the direction changes along a certain main axis, or at least one of the size and amplitude of the overshooting correction movements until the definitive positioning of the test mark.

3. The method as claimed in claim 1, wherein test procedures are begun along the same main axis with different offset of the alignment mark in each case along the connecting straight line.

4. The method as claimed in claim 3, wherein an image of the user or an eyepatch used by the user is additionally registered as a parameter, and items of information about the eye used or the user carrying out the experiment are used for the analysis.

5. The method as claimed in claim 1, wherein the outer marks and the alignment mark are strokes or circles having a length or diameter, respectively, in the range of 1-10 mm, and in the case of strokes having a stroke thickness in the range of 0.5-5 mm.

6. The method as claimed in claim 1, wherein the user carries out the test series using only one eye,
- or wherein the electronic device ensures that the information displayed on the display screen can be perceived by only one eye.

7. The method as claimed in claim 1,
- wherein the user controls the displacement of the alignment mark by a direct or indirect interaction with the electronic device,
- wherein the interaction can be performed by means of a touch-sensitive display screen, body movements, or by speech, or a combination thereof, and
- wherein, if the display screen is a touch-sensitive display screen, the user either aligns the alignment mark directly by touching and displacing the alignment mark on the display screen, or does so with the aid of one or more displacement knobs which are depicted on the display screen.

8. The method as claimed in claim 1,
- wherein a qualitative analysis or a quantitative analysis is output on the display screen as a function of the determined visual acuity, or a notification that medical aid should be sought, or
- wherein the arrangement of the outer marks and the alignment mark is individually adapted for the various individual test procedures on the basis of the statistical analysis of the preceding measurements.

9. The method as claimed in claim 1, wherein the data ascertained in a test series, without or in combination with items of information about the user, in personalized or anonymized form, are transmitted to a central office, and at the central office the data are at least one of stored, further processed, and relayed for at least one of information and further processing to medical support.

10. The method as claimed in claim 1, wherein the electronic device additionally has sensors, and thus determines the behavior of the user.

11. The method as claimed in claim 1, wherein the electronic device is a portable device, including a PDA, smartphone, mobile telephone, tablet, laptop, smart watch, data spectacles, or head-mounted display.

12. The method as claimed in claim 1,
wherein the results of various successively carried out test series, are evaluated relative to one another in the development thereof by at least one of the electronic device and a central computer and the development of the visual acuity is determined, and upon reaching a threshold value of a variable computed from the test series, a warning is output to the user or transmitted via an interface to a central office for making contact with the user, and/or
wherein the electronic device prompts the user, in the scope of a predefined time plan, to carry out a test series in each case at a certain point in time, and/or
wherein in the determination of the visual acuity, variations which are not caused solely by the mere visual acuity, are substantially or completely eliminated; and/or
wherein variations not caused solely by the mere visual acuity, including variations depending on the form on the day, are taken into consideration in the analysis.

13. The method as claimed in claim 1,
wherein the measurement data of the electronic device are transmitted to a central computer and analyzed therein using algorithms,
wherein the results of such analyses can be processed as personalized feedback, and provided to the user, and the results can be used to individualize the measuring arrangement, and
wherein the individualization can consist in a change of the measurement axes, the measurement points, the measurement interval, and the assessment of the measured values.

14. A portable electronic device for carrying out a method as claimed in claim 1, having a display screen and a data analysis unit.

15. A data processing program for carrying out a method as claimed in claim 1 on a portable electronic device having a display screen and a data analysis unit.

16. The method as claimed in claim 1,
wherein in the scope of one test series, at least two or at least three test procedures are carried out along the vertical main axis and two or at least three test procedures are carried out along the horizontal main axis, and/or at least two or at least three test procedures are carried out in each case along at least one of the two diagonal main axes,
wherein in the case of weaknesses of the user registered along certain main axes, these main axes are measured or subsequently only measured substantially exclusively, or wherein conclusions are drawn about the capacities of certain areas in the retinal region from the visual capacity determined along certain main axes, and
wherein these areas are defined in the polar grid of a polar coordinate system as circular sectors or circular ring sectors.

17. The method as claimed in claim 1,
wherein test procedures are begun along the same main axis with different offset of the alignment mark in each case along the connecting straight line, wherein an offset of ⅓, ½, and ⅔ of the distance between the two outer marks is specified along each main axis at the beginning of the respective test procedure, and
wherein the number of the individual test procedures or the respective offset are adapted individually on the basis of previous test series or preceding morphological examinations.

18. The method as claimed in claim 1,
wherein the outer marks and the alignment mark are strokes or circles having a length or diameter, in the range of 2-4 mm, and in the case of strokes having a stroke thickness in the range of 1-2.5 mm,
wherein all strokes are aligned parallel to the main axis to be measured during the entire test procedure,
wherein the size of the outer marks and the alignment mark are equal, and the marks are adapted in the size thereof to the visual acuity of the test person, or
wherein at least one of the following setting parameters is individually adapted on the basis of prior test series or prior individual test procedures or preceding morphological examinations: the size of the marks; the contrast on the display screen, the color selection on the display screen; optionally additionally provided focusing aids, wherein the individualization can be performed for each specific eye of the user.

19. The method as claimed in claim 1,
wherein the user controls the displacement of the alignment mark by a direct or indirect interaction with the electronic device,
wherein the interaction can be performed by means of a touch-sensitive display screen, body movements, of the hand or the head, or by speech, or a combination thereof, and
wherein, if the display screen is a touch-sensitive display screen, the user either aligns the alignment mark directly by touching and displacing the alignment mark on the display screen, or does so with the aid of one or more displacement knobs which are depicted on the display screen.

20. The method as claimed in claim 1, wherein the data ascertained in a test series, without or in combination with items of information about the user, in personalized or anonymized form, are transmitted to a central office, via an Internet or mobile telephone connection, and at the central office the data are stored, further processed, or relayed for information or further processing to medical support.

21. The method as claimed in claim 1,
wherein the electronic device additionally has sensors, in the form of a camera oriented toward the user, and thus determines the behavior of the user, including at least one of the spacing of the user from the display screen, and the eye spacing, and whether the test procedure is carried out in a monocular or binocular manner, and in the first case, which eye is closed in this case, or the rotation of the display screen about the vision axis or the orthogonality of the vision axis to the surface of the display screen and enables this to be incorporated into the data analysis or transmits a notification via the display screen to the user to set the corresponding variable to the correct value and/or to dynamically adapt, the display occurring on the display screen of outer marks and alignment mark on the basis of these items of information.

22. The method as claimed in claim 1, wherein the electronic device is a portable device, in the form of a PDA, smartphone, mobile telephone, tablet, laptop, smart watch, data spectacles, or head-mounted display.

23. The method as claimed in claim 1,
wherein the results of various successively carried out test series carried out on different days, are evaluated relative to one another in the development thereof by the electronic device or a central computer and the development of the visual acuity is determined, and upon reaching a threshold value of a variable computed from the test series, a warning is output to the user and/or transmitted via an interface to a central office for making contact with the user, and/or wherein the electronic device prompts the user, in the scope of a predefined time plan, to carry out a test series in each case at a certain point in time, wherein, depending on the result of a preceding test series and depending on changes of the results of the immediately preceding test series in relation to the base value determined by multiple preceding test series, a renewed test series is recommended to the user in the scope of a fixed time scheme, which can be every 3-14 days, or every 7 days, or, in the event of an established worsening of the results, after only an individually shortened time interval, and/or wherein in the determination of the visual acuity, variations which are not caused solely by the mere visual acuity, including variations depending on the form on the day, are substantially or completely eliminated, wherein this is performed by corresponding consideration of the time which the user has required for the displacement of the alignment mark or the number of direction changes during the displacement of the alignment mark by the user; and/or wherein upon the use of the determined visual acuity for inference about the state of the user, in the context of a test for response capacity, including determination of the influence of drugs or medications, variations not caused solely by the mere visual acuity, including variations depending on the form on the day, are taken into consideration in the analysis, and wherein this can be performed by corresponding consideration of the time which the user has required for the displacement of the alignment mark or the number of direction changes during the displacement of the alignment mark by the user, or by further parameters determined by sensors of the device.

24. The method as claimed in claim 1,
wherein the measurement data of the electronic device are transmitted to a central computer and analyzed therein using algorithms:
i) the variance increase of the measurement point spacings relative to a comparative measurement;
ii) the consideration of patient characteristics, including age, sex, ophthalmological findings including eyesight, eye diseases, and systemic diseases; and
iii) subjectively experienced degree of difficulty of carrying out the test, test duration, amount and amplitude of the control and correction of the test mark and the progression of the test results, mobility behavior of the user, and any possible therapeutic measures, wherein the results of such analyses can be processed as personalized feedback, with our without individualization for each eye, and provided to the user, and the results can be used to individualize the measuring arrangement, and wherein this individualization can consist in a change of the measurement axes, the measurement points, the measurement interval, and the assessment of the measured values.

25. A portable electronic device for carrying out a method as claimed in claim 1, having a display screen and a data analysis unit, wherein the display screen is a touch-sensitive display screen, and wherein the electronic device additionally has a camera oriented toward the user.

26. A data processing program product comprising a non-transient storage medium carrying a program for carrying out a method as claimed in claim 1 on a portable electronic device having a display screen and a data analysis unit, in the form of a mobile application (app).

27. A method for determining the visual acuity of a user, in which, in the scope of a plurality of individual test procedures carried out in succession and conducted in the manner of a test series, in the scope of each individual test procedure, two spaced-apart outer marks, which are fixed within an individual test procedure, and an alignment mark located therebetween but not on a connecting straight line of the outer marks, are displayed to the user on a display screen of an electronic device, and the user is prompted, by actuating the electronic device, to displace the alignment mark on the display screen exclusively perpendicularly to the connecting straight line of the outer marks until in the perception of the user the alignment mark lies on the connecting straight line, and subsequently, after completed displacement of the alignment mark by the user, the electronic device registers at least one of the following parameters:
the effective spacing of the alignment mark from the connecting straight line after displacement of the alignment mark by the user;
the time which the user has required for the displacement of the alignment mark; and
the number of direction changes during the displacement of the alignment mark by the user, wherein at least two or at least three individual test procedures are carried out, in which the outer marks are arranged along a same main axis or previously determined auxiliary axes, and wherein the tests are measured with the outer marks arranged along at least two different main axes in the scope of one test series, wherein the at least one registered parameter or, upon measurement of multiple parameters, a combination of the registered parameters is used as a measure for determining the visual acuity from the individual test procedures of the test series, and wherein test procedures are begun along a same main axis with different offset of the alignment mark in each case along the connecting straight line.

28. The method as claimed in claim 27, wherein in the scope of one test series, at least three test procedures are carried out along the vertical main axis and at least three test procedures are carried out along the horizontal main axis, and/or at least two or at least three test procedures are carried out in each case along at least one of the two diagonal main axes.

29. The method as claimed in claim 27, wherein test procedures are begun in each dimension in each experiment with the same distance between the outer marks.

30. A method for determining the visual acuity of a user, in which, in the scope of a plurality of individual test procedures carried out in succession and conducted in the manner of a test series, in the scope of each individual test procedure, two spaced-apart outer marks, which are fixed within an individual test procedure, and an alignment mark located therebetween but not on a connecting straight line of the outer marks, are displayed to the user on a display screen of an electronic device, and the user is prompted, by actuating the electronic device, to displace the alignment mark on the display screen perpendicularly to the connecting straight line of the outer marks until in the perception of the user the alignment mark lies on the connecting straight line, and subsequently, after completed displacement of the alignment mark by the user, the electronic device registers at least one of the following parameters:

the effective spacing of the alignment mark from the connecting straight line after displacement of the alignment mark by the user;

the time which the user has required for the displacement of the alignment mark; and the number of direction changes during the displacement of the alignment mark by the user, wherein at least two or at least three individual test procedures are carried out, in which the outer marks are arranged along a same main axis or previously determined auxiliary axes, and wherein the tests are measured with the outer marks arranged along at least two different main axes in the scope of one test series, wherein the at least one registered parameter or, upon measurement of multiple parameters, a combination of the registered parameters is used as a measure for determining the visual acuity from the individual test procedures of the test series, and wherein test procedures are begun in each dimension in each experiment with the same distance between the outer marks and along a same main axis with different offset of the alignment mark in each case along the connecting straight line.

31. The method as claimed in claim 30, wherein the user is prompted, by actuating the electronic device, to displace the alignment mark on the display screen exclusively perpendicularly to the connecting straight line of the outer marks until in the perception of the user the alignment mark lies on the connecting straight line.

* * * * *